US00PP20223P2

(12) United States Plant Patent
Li

(10) Patent No.: US PP20,223 P2
(45) Date of Patent: Aug. 18, 2009

(54) ***VERBENA* PLANT NAMED 'KLEVP07355'**

(50) Latin Name: ***Verbena* hybrid**
Varietal Denomination: KLEVP07355

(75) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/080,403

(22) Filed: Apr. 2, 2008

(51) Int. Cl.
*A01H 5/00* (2006.01)

(52) U.S. Cl. ..... Plt./308

(58) Field of Classification Search ..... Plt./308
See application file for complete search history.

*Primary Examiner*—Susan B McCormick Ewoldt
(74) *Attorney, Agent, or Firm*—Jondle & Associates, P.C.

(57) ABSTRACT

A new cultivar of *Verbena* particularly characterized by purple flowers with small white eyes, good resistance to powdery mildew and a good branching habit, is disclosed.

1 Drawing Sheet

Genus and species: *Verbena* hybrid.
Variety denomination: 'KLEVP07355'.

BACKGROUND OF THE NEW PLANT

The present invention comprises a new and distinct cultivar of *Verbena,* botanically known as *Verbena* hybrid, and hereinafter referred to by the cultivar name 'KLEVP07355'. 'KLEVP07355' was discovered as a seedling resulting from a cross conducted in fall 2003 in Cobbitty, Australia between the proprietary female *Verbena* parent, '00.699.10' (unpatented) and the proprietary male *Verbena* parent, '00.645.60' (unpatented). A single plant selection was subsequently chosen for further evaluation and for asexual propagation.

The new cultivar was created in 2003 in Cobbitty, Australia and has been asexually reproduced repeatedly by vegetative cuttings in Stuttgart, Germany over a four and one-half-year period (approximately 6 to 8 generations). 'KLEVP07355' has been found to retain its distinctive characteristics through successive asexual propagations.

SUMMARY OF THE INVENTION

The following are the most outstanding and distinguishing characteristics of this new cultivar when grown under normal commercial practices in a greenhouse in Stuttgart, Germany.

1. Purple flowers with small white eyes;
2. Good resistance to powdery mildew; and
3. A good branching habit.

DESCRIPTION OF THE PHOTOGRAPH

This new *Verbena* plant is illustrated by the accompanying photograph which shows a close-up of the mature inflorescence and foliage; the colors shown are as true as can be reasonably obtained by conventional photographic procedures. The photograph is of a plant about 4-months old and grown from rooted cuttings in an 18-cm pot in a greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEVP07355'. The data which define these characteristics were collected from asexual reproductions carried out in Stuttgart, Germany. The plant history was taken on 4-month old plants in 18-cm pots that were pinched once approximately two weeks after potting and grown in a greenhouse. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Verbenaceae.
- *Genus and species.*—*Verbena* hybrid.
- *Common name.*—*Verbena.*

Parentage:
- *Female parent.*—The proprietary *Verbena* parent, '00.699.10' (unpatented).
- *Male parent.*—The proprietary *Verbena* parent, '00.645.60' (unpatented).

Plant:
- *Growth and branching habit.*—Good branching.
- *Outdoor performance.*—For use as a bedding plant and in baskets.
- *Height (from top of soil).*—5.0 cm.
- *Width (horizontal plant diameter).*—35.0 cm.
- *Time to produce a finished flowering plant.*—13 weeks from sticking of unrooted cuttings.
- *Time to initiate and develop roots.*—3 weeks.
- *Root description.*—Fine and fibrous.

Stems:
- *Number of branches per plant.*—Greater than 10.
- *Length.*—About 15.0 cm.
- *Diameter (measured from the midpoint).*—17.0 cm.
- *Internode length.*—About 2.5 cm.
- *Color.*—RHS 140C.
- *Anthocyanin.*—RHS 140C.
- *Texture.*—Pubescent.

Leaves:

*Arrangement.*—Opposite.

*Color, immature leaf* (*both upper and lower surface*).—RHS 135C.

*Color, mature leaf* (*both upper and lower surface*).—RHS 135B.

*Length.*—3.5 cm.

*Width.*—2.0 cm.

*Shape.*—Cordate.

*Apex.*—Cuspidate.

*Base.*—Wide, open.

*Margin.*—Crenate.

*Texture.*—Smooth.

*Venation.*—Pinnate.

*Venation color.*—RHS 135B.

*Petioles.*—Length: Less than 0.5 cm. Diameter: Less than 0.3 cm. Color: RHS 140C. Texture: Pubescent.

Flower bud:

*Shape.*—Tall, cylindrical.

*Length.*—Up to 1.5 cm.

*Diameter.*—Less than 0.2 cm.

*Color* (*at tight bud*).—RHS 140C.

Inflorescence:

*Blooming habit* (*flowering season*).—Spring to fall (April to December).

*Lastingness of individual blooms on the plant.*—Approximately 3 weeks.

*Fragrance.*—Absent.

*Inflorescence shape.*—Fan-shaped.

*Length of inflorescence.*—2.0 cm.

*Diameter of inflorescence.*—2.0 cm.

*Number of florets per inflorescence.*—Greater than 25.

*Peduncle.*—Length: About 2.0 cm. Diameter: Less than 0.2 cm. Color: RHS 140C. Texture: Pubescent.

Florets:

*Floret form.*—Radial.

*Floret length.*—About 0.7 cm.

*Floret diameter.*—About 1.5 cm.

*Color, immature flower.*—Upper surface: RHS 78C. Lower surface: RHS 77C.

*Color, mature flower.*—Upper surface: RHS 77B. Lower surface: RHS 77D.

*Corolla tube length.*—0.5 cm.

*Corolla tube color.*—RHS 70D.

*Petals.*—Length of lobe: Less than 0.8 cm. Diameter of lobe: Less than 0.1 cm. Lobe shape: Tall, cylindrical. Apex: Obtuse. Base: Round. Margin: Smooth.

*Pedicels.*—Length: Greater than 1.5 cm. Diameter: Greater than 0.1 cm. Color: RHS 70D. Texture: Smooth.

Calyx:

*Sepals.*—Shape: Cylindrical. Length: Greater than 1.0 cm. Diameter: Greater than 0.2 cm. Color: RHS 135C. Apex: Cuspidate. Base: Obtuse. Margin: Crenate. Texture: Satiny.

Reproductive organs:

*Stamens.*—Quantity: Many. Color: Creamy white. Filament length: Less than 0.1 cm. Filament diameter: Less than 0.1 cm.

*Anther.*—Length: Less than 0.1 cm. Diameter: Less than 0.1 cm.

*Pollen.*—Amount: Unable to determined.

*Pistils.*—Number: 1. Length: 1.0 cm. Diameter: 0.1 cm.

*Stigma.*—Color: Creamy white. Shape: Round. Length: Less than 0.1 cm. Diameter: Less than 0.1 cm.

*Style.*—Color: Creamy white. Length: Less than 0.1 cm. Diameter: Less than 0.1 cm. Shape: Ovate.

Fruit and seed set: None observed.

Disease and insect resistance: Not observed.

COMPARISON WITH PARENTAL AND COMMERCIAL CULTIVARS

'KLEVP07355' differs from the female parent, the proprietary '00.699.10' (unpatented) in that 'KLEVP07355' has purple flowers with small white eyes, while '00.699.10' has purple flowers.

'KLEVP07355' differs from the male parent, the proprietary '00.645.60' (unpatented) in that 'KLEVP07355' has purple flowers with small white eyes, while '00.645.60' has burgundy flowers with big eyes.

'KLEVP07355' differs from the commercial comparison variety 'KLEVP06349', also known as 'Fuego Denim Blue' (U.S. Plant patent appl. Ser. No. 12/005,104) in that 'KLEVP07355' has purple flowers with small white eyes, while 'KLEVP06349' has blue flowers.

I claim:

1. A new and distinct cultivar of *Verbena* plant as shown and described herein.

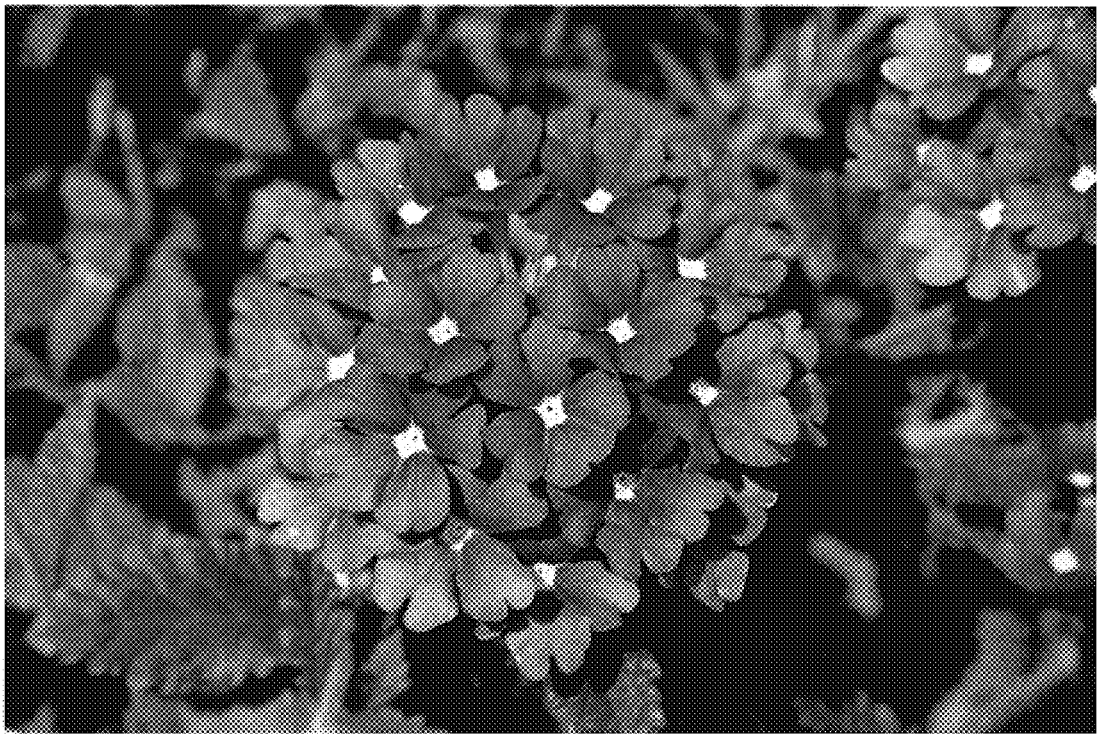

* * * * *